United States Patent
Wang et al.

(10) Patent No.: US 10,082,501 B2
(45) Date of Patent: Sep. 25, 2018

(54) NANOTUBE BASED LATERAL FLOW DEVICE FOR BIOMARKER DETECTION

(71) Applicant: BioMedomics, Inc., Durham, NC (US)

(72) Inventors: Xue-feng Wang, Chapel Hill, NC (US); Qingqi Chen, Chapel Hill, NC (US)

(73) Assignee: BioMedomics, Inc., Durham, NC (US)

( * ) Notice: Subject to any disclaimer, the term of this patent is extended or adjusted under 35 U.S.C. 154(b) by 1247 days.

(21) Appl. No.: 13/934,707

(22) Filed: Jul. 3, 2013

(65) Prior Publication Data

US 2014/0287526 A1   Sep. 25, 2014

Related U.S. Application Data

(60) Provisional application No. 61/804,684, filed on Mar. 24, 2013.

(51) Int. Cl.
    *G01N 33/558*     (2006.01)
(52) U.S. Cl.
    CPC .................................. *G01N 33/558* (2013.01)
(58) Field of Classification Search
    CPC .................................................... G01N 33/558
    See application file for complete search history.

(56) References Cited

U.S. PATENT DOCUMENTS

| | | | |
|---|---|---|---|
| 6,136,610 A | 10/2000 | Polito et al. | |
| 8,716,029 B1* | 5/2014 | Kim | G01N 33/5306 436/501 |
| 2006/0040318 A1* | 2/2006 | Melker | B82Y 5/00 435/7.1 |
| 2006/0240492 A1* | 10/2006 | Rusling | G01N 33/551 435/7.23 |
| 2008/0185295 A1* | 8/2008 | Briman | G01N 33/5438 205/777.5 |

(Continued)

FOREIGN PATENT DOCUMENTS

WO   WO 97/09620   3/1997

OTHER PUBLICATIONS de la Rica et al., "Label-Free Pathogen Detection with Sensor Chips Assembled from Peptide Nanotubes", Angew. Chem. Int. Ed. (2008), 47:9752-9755.*

(Continued)

*Primary Examiner* — Scott Long
*Assistant Examiner* — Gary E Hollinden
(74) *Attorney, Agent, or Firm* — Jenkins, Wilson, Taylor & Hunt, P.A.

(57) ABSTRACT

Nanotube based lateral flow test device described herein is a lateral flow based diagnostic device, which uses arrays of fragments of single wall carbon nanotubes as sensor to detect the biomarkers at ultralow concentration (below picogram per milliliter). The device is consisted of the following components: (1). an lateral flow strip which typically is consisted of a backing film laminated with conjugate/sample pads, nitrocellulose membrane, wicking pad, (2). the arrays of single wall carbon nanotube conjugate with antibody which is immobilized on the membrane of the lateral flow device as the test line, (3). pairs of micro-electrode are installed on top part of the cassette, (4). a cassette which holds the lateral flow strip. The device can be used in clinical environments for biomarker detection.

11 Claims, 5 Drawing Sheets

(56) References Cited

U.S. PATENT DOCUMENTS

| | | | | |
|---|---|---|---|---|
| 2009/0218239 A1* | 9/2009 | Gooding | ............ | G01N 33/542 |
| | | | | 205/792 |
| 2011/0223689 A1* | 9/2011 | Bailey | ............ | G01N 33/54306 |
| | | | | 436/506 |
| 2014/0220706 A1* | 8/2014 | Belbruno | ............... | G01N 27/06 |
| | | | | 436/501 |
| 2014/0377789 A1* | 12/2014 | Moerman | .......... | G01N 33/5438 |
| | | | | 435/14 |

OTHER PUBLICATIONS

Kang et al., "High performance electronics using dense, perfectly aligned arrays of single-walled carbon nanotubes," Nature Nanotechnology 2, No. 4, 230-236 (2007).

* cited by examiner

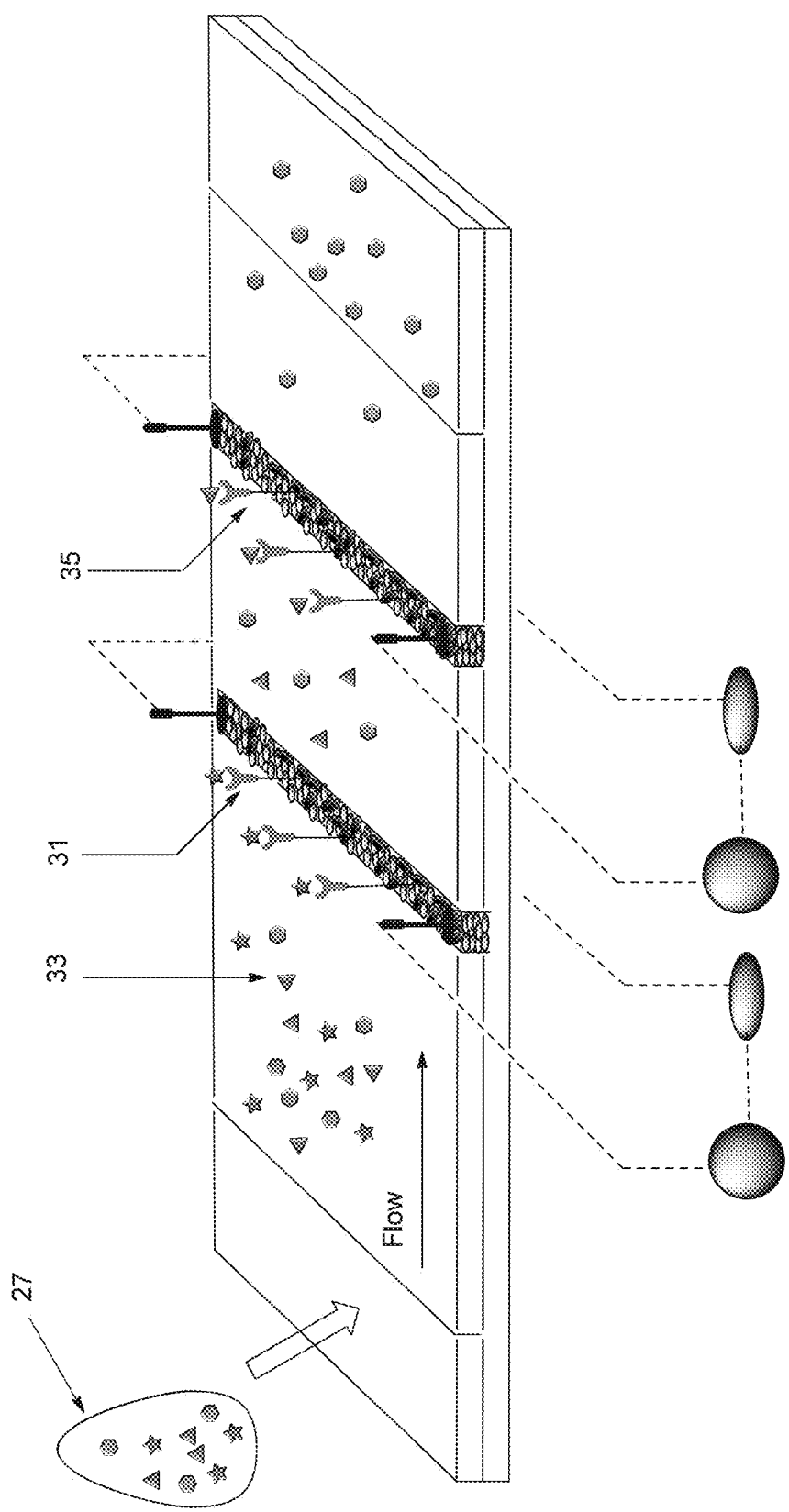

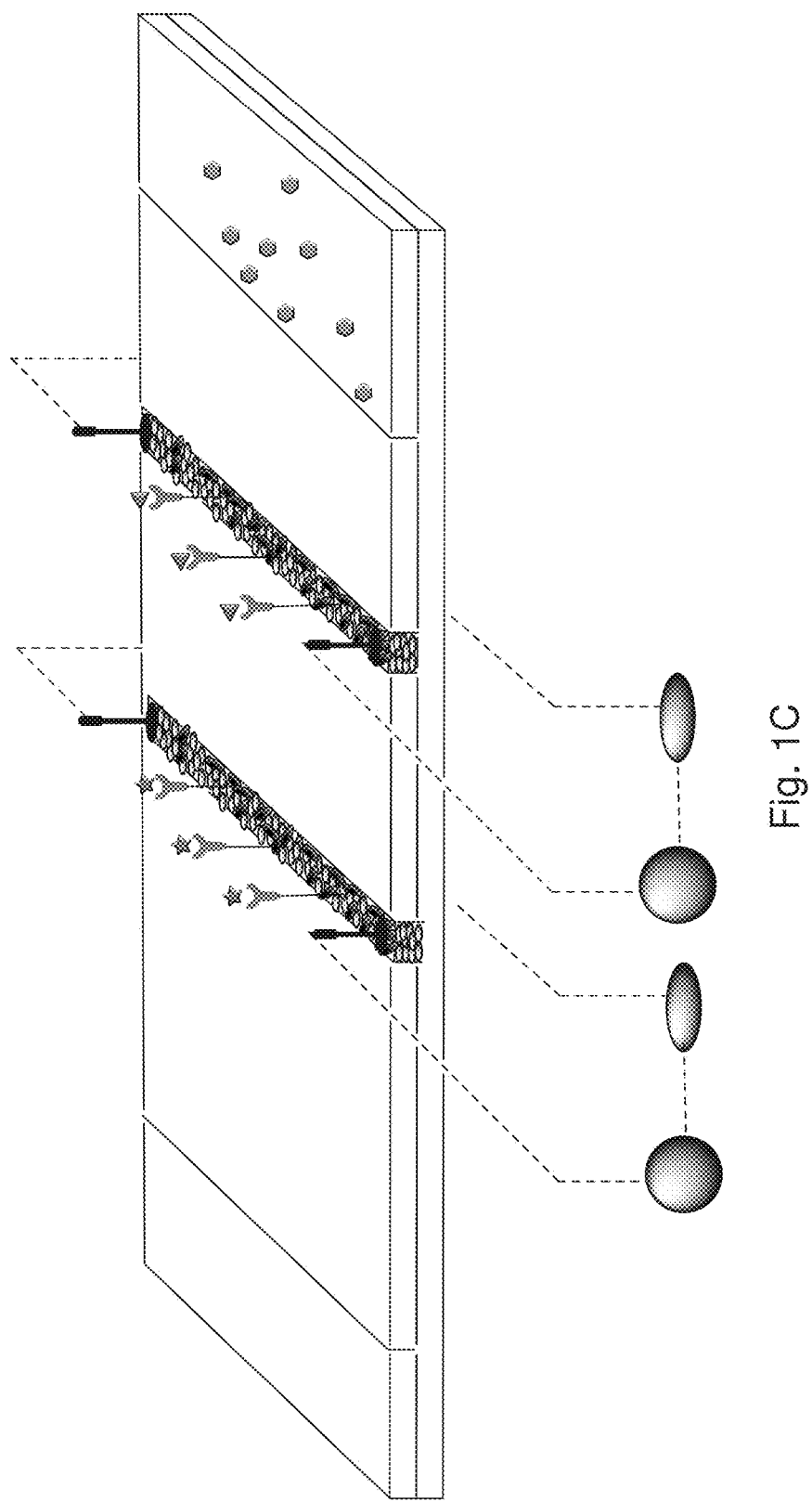

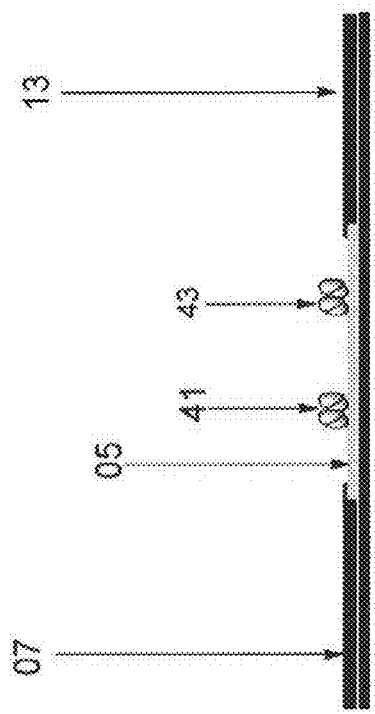
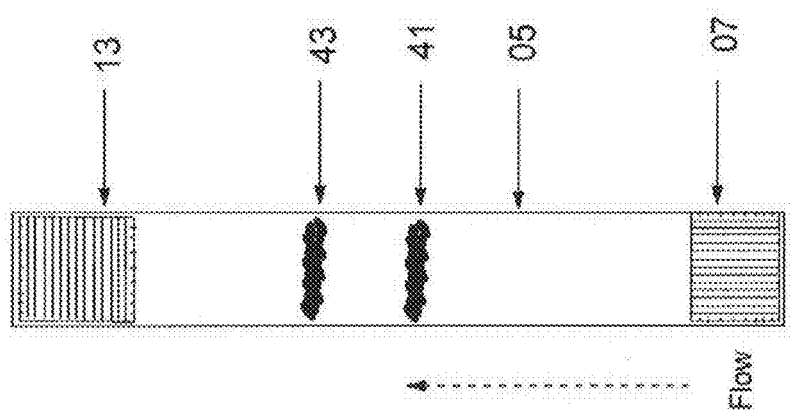

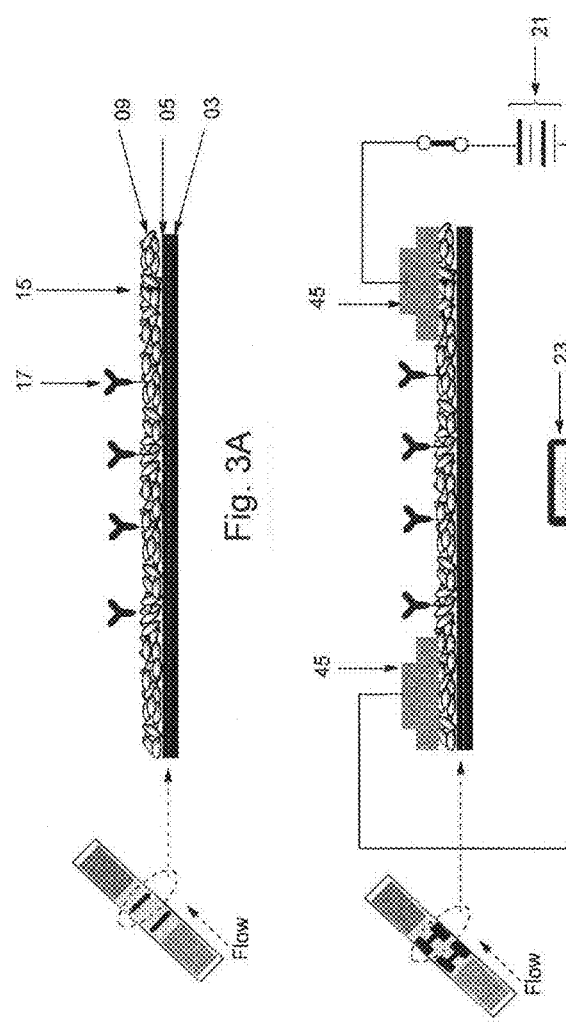
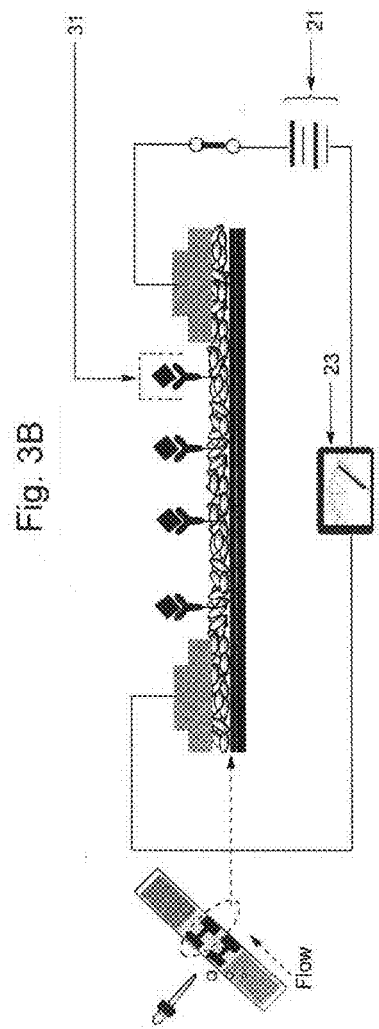
Fig. 3A
Fig. 3B
Fig. 3C

US 10,082,501 B2

NANOTUBE BASED LATERAL FLOW DEVICE FOR BIOMARKER DETECTION

BACKGROUND

Lateral flow immunoassay (LFIA) technology has seen commercial success in recent years because of its simplicity, low cost and user friendliness. The technology is particularly suitable for point-of-care (POC) test markets. It has been utilized for detection of a large number of analytes from small molecules, enzymes, macromolecules to microorganisms. One or several analytes can be tested for simultaneously on the same strip. Urine, saliva, serum, plasma, or whole blood can be used as specimens. Extracts of patient exudates or fluids have also been successfully developed. Lateral flow tests, or immunochromatographic strips, were first introduced as qualitative urine pregnancy tests used in doctors' offices and at home. They have evolved into rapid tests for a range of analytes, including HIV, respiratory diseases, drugs-of-abuse, cardiac markers and infectious diseases.

Lateral flow tests are a form of immunoassay in which the test sample flows along a solid substrate via capillary action. After the sample is applied to the test strip, it encounters a colored reagent, which mixes with the sample and transits the substrate encountering lines or zones which have been pretreated with an antibody or antigen. Depending upon the analytes present in the sample, the colored reagent can become bound at the test line or zone. Recent improvements in lateral-flow testing have been made using both fluorescent and magnetic labels. Lateral flow tests can operate as either competitive or sandwich assays. Although their use has become widespread, lateral-flow tests have sensitivity limitations and tend to be semi-quantitative.

Researchers have developed the technology for analyte quantification (See for example, Rylant, D.; Moss, D.; Jane, A.; Bundesen, P., WO97/09620, 1997 and Polito, A.; Thayer, R. M.; DiNello, R. K.; Sierra, G. H.; Nixon, D.; Phillips, A.; Neubarth, S. U.S. Pat. No. 6,136,610, 2000). A number of platforms have been pursued using different particles and various detection techniques. Colored particles, quantum dots, fluorescent latex particles, liposome-based probes, magnetic particles, and Raman-active tags. Each of these detection techniques has its advantages and shortcomings. Absorbance based detection techniques often lack desirable detection sensitivity, while fluorescence techniques often require complex and expensive instrumentation. Lateral flow devices for magnetic-field measurements cannot be sealed inside a plastic housing, making it very difficult to use in POC markets. Like conventional fluorescence, Raman-based detection technology also needs expensive instruments.

Although, the current lateral flow test technologies are very useful because they are easy to use, there are many drawbacks related to current (or traditional) lateral flow tests. Most importantly, the current LFIA testing sensitivity is limited. In the lateral flow assay, gold particles, dyes or latex beads are used. These additional labeling, conjugation, and optical sensing steps are complicated which increase the manufacturing cost and testing cost Sensitive systems for detecting biomarkers, known as biosensors, are valuable for early detection of initial onset of disease, or for monitoring post-treatment monitoring to detect recurrence of diseases. Biosensors, which can convert chemical or biological events into measurable signals, have two key components: 1) the recognition component and 2) the transducing/reporting component. The recognition component is responsible for carrying out specific interactions with the target molecules while the transducing/reporting component is responsible to convert the changes caused by the binding of target molecules into a signal that can be recorded. Such a signal can be mechanical, optical, electrochemical or electrical.

BRIEF DESCRIPTION OF THE INVENTION

A first aspect of the present invention is the lateral flow immunoassay device having one or more arrays comprised of small fragments of single wall carbon nanotubes to which are conjugated antibodies for a certain biomarker. Typically, the fragments range in length from about 2 to about 6 μm with the fragments in close proximity to each other so that each array is capable of conducting an electric current, and the device is capable of detecting the presence and amount of the biomarker at pictogram/mL and fermtogram/mL concentrations in a biological sample.

In one embodiment, the device comprises a lateral flow assay system having a sample pad at one end and a wicking pad at the opposite end, a first array of single wall carbon nanotubes in the form of bands to which is conjugated antibodies to the biomarker to be assayed forming a test line proximal to the sample pad, and a second array of single wall carbon nanotubes fragments in the form of bands to which is conjugated non discriminate antibodies forming a control line between the first array and the wicking pad. The system further having a means to pass an electric current through the first and second arrays independently and a means of independently measuring changes in the current in the two arrays.

In a second embodiment of the invention of the first aspect, the device of the first embodiment further has a means of recording the independent changes in current passing in the two arrays.

A second aspect of the present invention is a method of determining the amount of a certain biomarker present in a sample of analyte using the device of the first aspect.

A third aspect of the present invention is a method of constructing the device of the first aspect.

BRIEF DESCRIPTION OF THE DRAWINGS

FIG. 1B. Schematic perspective view of nanotube based lateral flow assay depicted in FIG. 1A showing initiation of the assay process.

FIG. 1C. Schematic perspective view of nanotube based lateral flow assay depicted in FIG. 1A shown at completion of the assay process.

FIG. 2A. Schematic top view of nanotube based lateral flow assay showing the relation of flow zones and nanotube bands.

FIG. 2B. Cross sectional schematic view of nanotube based lateral flow assay along the longitudinal axis showing relation of flow zones and nanotube bands.

FIG. 3A. Cross sectional schematic view of nanotube based lateral flow assay along the latitudinal axis without electrical elements.

FIG. 3B. Cross sectional schematic view depicted in FIG. 3A showing electrical elements FIG. 3C. Cross sectional schematic view depicted in FIG. 3B showing electrical current across a nanotube fragment array when biosensors conjugate with antibodies attached to the array.

DETAILED DESCRIPTION OF THE INVENTION

Figure 1A:
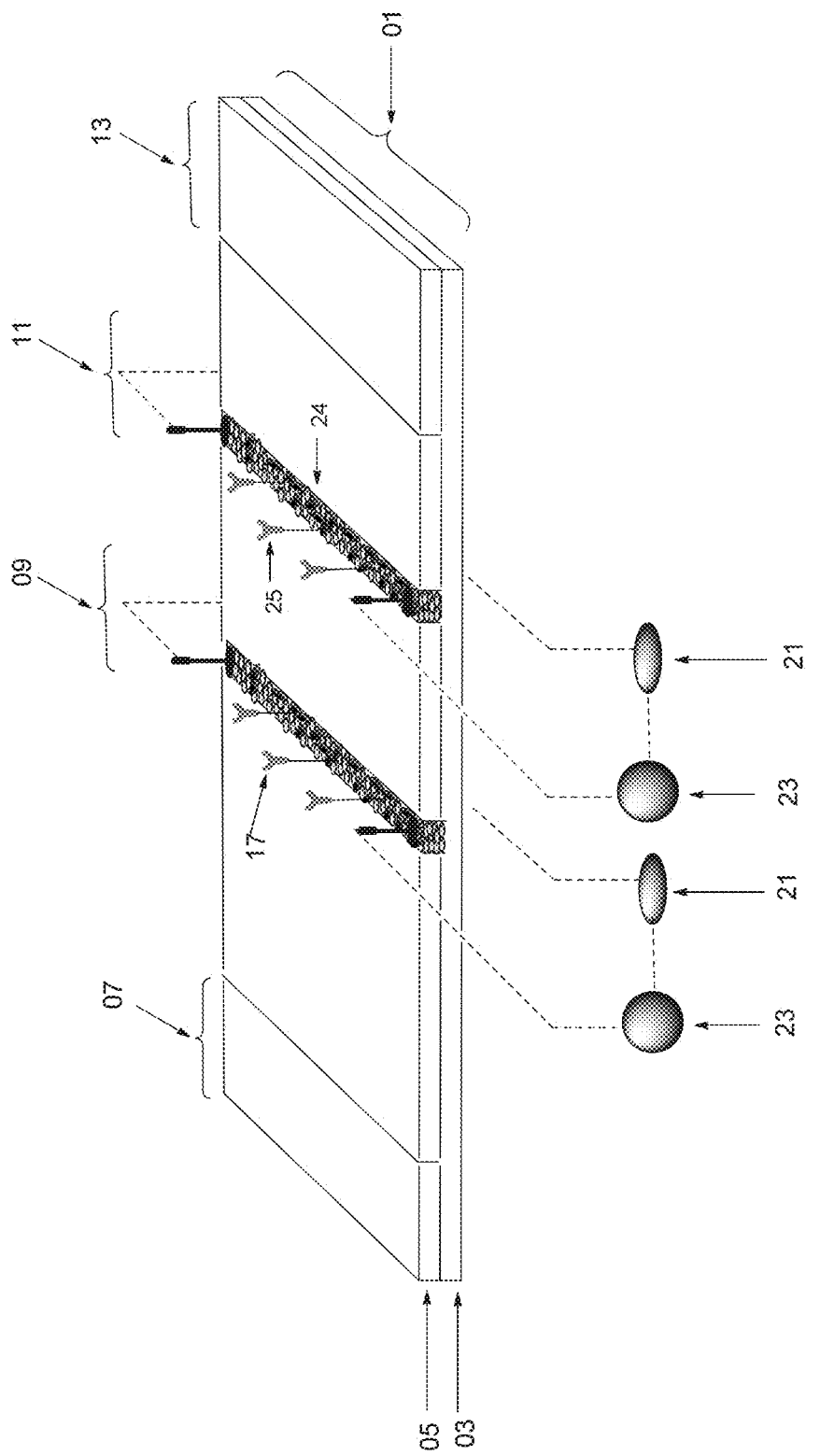
FIG. 1A. Schematic perspective view of nanotube based lateral flow assay showing its elements.

The biosensors presented herein focus on nanoscale biosensors with substantial modulation in conductivity upon target binding. A common way to prepare conductivity based chemical and biological sensors is to modify bulk semiconductor devices, such as field effect transistors (FETs), with molecular receptors. When the target molecules bind to the receptors, the charge transfer between the target molecules and receptors leads to either depletion or accumulation of carriers within the device structure, causing a detectable change in the conductance.

Using nanometer scale electronic devices, i.e. nanometer scale FETs (also referred to herein as "nanoelectronic devices"), for sensing, the total number of carriers involved in the conduction in nanoelectronic devices is much smaller than their bulk equivalents. Consequently, a small change in the total number of carriers will have a big effect on the device properties. Therefore, the sensitivity of the nanoscale sensors can be significantly improved compared to bulk devices. For example, sensors based on semiconducting Si nanowires can function as pH sensors, highly sensitive protein sensors, and metal ion sensors when the nanowires are modified with specific recognition functional groups. The sensitivity of the devices can be so high that binding of individual molecules on the devices can be monitored by change in conductivity.

The nanosensor materials taught herein are fragments of carbon nanotubes that are hollow tubes that consist of one or more graphene sheets (layers of graphite) wrapped seamlessly into cylinders to form seamless nanotubes. While the diameters of these nanotubes are typically in the nanometer range, the lengths can be in the micro meter range. However, carbon nanotubes are fragile, so that consistently producing long nanotubes is difficult. Thus, carbon nanotubes biological sensors of the art are expensive, and therefore, are not well suited for point of care LFIA, which need to be disposable and inexpensive. The present invention teaches that arrays of small fragments of carbon nanotubes are suitable for biosensors in LFIA devices and can be produce inexpensively. The fragments of nanotubes taught herein are in the range of about 2 to about 6 µm and are arrayed in close proximity so that each fragment touches adjacent fragments sufficiently so that the array, as a unit, is capable to conducting an electrical current.

The vector that represents the circumference of a single walled nanotube must be a lattice vector in a two dimensional graphene plane. A nanotube is named by this lattice vector (n,m) which also determines the diameter and helicity of the nanotube. Importantly, carbon nanotubes can be either metallic or semiconductive depending on their helicity and diameter. If n=m, the nanotube is metallic. For nanotubes with n−m=3i, where i is an integer, the nanotubes are small band-gap semiconductors. All other nanotubes are moderate band-gap semiconductors.

The arrays of semiconducting carbon nanotube fragments in close proximity used in the present invention are sensitive, and in some case, very sensitive, to the surrounding environment. For example, the presence of oxygen, $NH_3$ and many other molecules, including large biological molecules such as proteins that can either donate or remove electrons from the nanotubes can significantly change the conductivity of the nanotubes. This sensitivity makes semiconducting carbon nanotubes FETs ideal candidates for nanoscale sensing materials, because they can function as gas sensors and biosensors. However, typically these nanotubes must be shielded except the portion designed for detection of a specific material to avoid interference of environmental elements noted above. Polymers such as BSA, PEG-3000, and PVA may be used to provide the shielding. Details of shielding is taught herein below in Scheme 1 and Example 6.

Receptor proteins that are found in virtually all biological systems recognize and bind specific molecules such as drugs, toxins, hormones or other proteins. The binding of these molecules to their receptors can be detected using carbon nanotube FETs that have been functionalized with receptor proteins. Molecules that bind to their receptors produce a characteristic change in the electronic properties or "signature" of a FET, such as conductivity. These molecules can be detected by reading the electronic signature produced by these devices with sensitive electronic measuring devices. However, prior to the present invention, there were some unsolved problems that limited the application of carbon nanotubes as sensors, including the synthetic methods of preparing nanotubes yield nanotubes with mixed helicities, resulting in a mixture of metallic and semiconducting nanotubes. Separation of the nanotubes according to their electronic properties is difficult.

To develop sensors that are only sensitive to specific target molecules, modification of the nanotube surfaces with molecular receptors is needed. However, the sidewalls of carbon nanotubes are chemically stable, making the fictionalization of the nanotubes with sensing elements a challenge. Moreover, covalent modification of the nanotube sidewalls can significantly change the electronic properties of the nanotubes, making them insulators rather than semiconductors. A reliable, non-covalent modification procedure for carbon nanotube sidewalls or a method to functionalize the surroundings of nanotubes is required for the development of carbon nanotube based nanosensors.

A single nanotube sensor is difficult to manufacture and is not likely to be sensitive enough for biomarker detection. As previously noted, nanotubes are quite fragile and often break into fragments during production. In order to make practical use of nanotube FETs as nanobiosensors, an array of aligned nanotubes has been used in the art to construct a wider area for sensing purposes which significantly increases detection sensitivity. Using Aligned Carbon Nanotubes (ACN) technologies, high density aligned single walled carbon nanotubes can be grown (see S. J. Kang, et al., *High-performance electronics using dense, perfectly aligned arrays of single-walled carbon nanotubes*, Nature Nanotechnology 2, no. 4, 230-236 (2007) and Q. K. Yu, et al., *Mechanism of horizontally aligned growth of single-wall carbon nanotubes on r-plane sapphire*, Journal of Physical Chemistry B 110, no. 45, 22676-22680 (2006)). The nanotubes can be transferred to any substrates such as Si substrates with preformed trenches. The aligned nanotube arrays have high current FET properties which is suitable for highly sensitive biosensing applications.

The present invention provides two major improvements over the current single walled nanotube-based detection systems of the art:

1) Fragments of single wall nanotubes, arrayed intimately in close proximity improve detection reproducibility by averaging the response from different single nanotubes. If individual nanotubes are used as is the case in the art, the response from each nanotube can be very different, causing problems in the reproducibility of the devices.
2) Comparing to single nanotubes used in devices of the art, small fragments of single wall nanotubes, arrayed intimately in close proximity, as is the case in the present invention, provide much higher sensitivity since each nanotube spans across the source and drain electrodes with more signals to detect.

The present nanotube invention is a device, which utilizes the principal of lateral flow immunoassay. The nanotube detection invention is assembled with the following components: (1) traditional lateral test strip; (2) nanotube-monoclonal antibody which is immobilized on the membrane of the strip; (3) a pair of electrodes are installed on two ends of the nanotube test line; (4) an electrical reader device to read electrical signals from test strip electrodes which can be later processed to biomarker detection.

Nanotube based biosensing is a very powerful tool. One distinct advantage of nanotube based lateral flow immunological assays is that it is label free of the antibody or the antigen (also referred to herein as the "analyte"), which is a characteristic that helps in the creation of a simple bioassay platform. It is an electrical signal detection that correlates with the immunoreaction allowing the detection of the analyte of interest. The lateral flow immunoassay architecture, because of its simplicity, reliability and low cost nature, has gained tremendous popularity for point-of-care diagnostic applications. Thus, Introducing nanotube sensing to lateral flow immunoassay technologies, generates a novel and surprisingly effective nanosensing assay platform for many clinical diagnosis applications.

FIG. 1A is a schematic depiction of the lateral-flow immunoassay system 01 of the present invention. Readers will find it convenient to have FIGS. 1A-1C before them to better understand this section. As is typical of the elements of an assay build on lateral flow architecture, the present system 01 comprises a rigid or semi-rigid backing 03, e.g. plastic or glass, which supports membrane layer 05, that is an inert, fibrous material capable of supporting movement of liquids by capillary action, and under certain conditions, binding biologically derived molecules such as proteins or antibodies. An example of such a fibrous material is nitrocellulose, which is widely used as LFIA membrane material. Optionally, membrane layer 05 may be comprised of one or more layers that may be of the same or different compositions. In the art of lateral-flow immunoassay systems, a strip of membrane, e.g. membrane layer 05, on a support 03 is often referred to as a "strip" or "card" and membrane strips or cards of various compositions are commercially available.

Membrane layer 05 is zoned into functional areas referred to herein as sample pad 07, test line 09, reference line (also referred to as "control line") 11, and wicking pad (also referred to as "absorbing pad") 13 arrayed in the order shown in FIG. 1A. Sample pad 07 and test line 09, test line 09 and reference line 11, and reference line 11 and wicking pad 13 are separated by flow zones. Note that the flow zone between sample pad 07 and test line 09 may also be referred to as the "conjugation zone" because in some assays, entities, e.g. antibodies and biomarkers, are conjugated with the analyte in this zone.

In the present invention, immobilized on the strip of membrane layer 05 that forms test line 09 is one or more close proximity arrays (also referred to as "bands") of fragments of nanotubes 15, to which are bound antibodies 17 that specifically conjugate with material, i.e. "the analyte," the particular assay is design to detect. (Note that in FIGS. 1A-1C the fragmented nature of is symbolically illustrated.) The use of arrayed fragments of nanotubes 15 bound to antibodies 17, i.e. biosensors, as the detection means distinguish the present invention over LFIA technology of the art. That is, a constant electrical current generated by power source 21 passes through aligned nanotubes 15 and changes in this electrical current are detected by electrical sensing means 23. In FIGS. 1A-1C, for simplicity of illustration, sensing means 23 is symbolized by a sphere, but may be any suitable current sensing device or system of devices. Likewise, the dotted lines represent electrical paths, e.g. wires connecting power source 21, electrical sensing means 23, and system 01. For identification of elements not expressly numbered in FIGS. 1B and 1C, the reader should refer to FIG. 1A. Details of the electrical connections and electronic components are presented in FIGS. 2A, 2B, and 3A-3C. For example, in the present invention, it is contemplated that information from sensing means 23 would be in communication with a computer for analysis, recordation, and automation. Likewise, immobilized on the strip of membrane layer 05 that forms reference line 11 is a close proximity array of fragments of nanotubes 24, to which is bound capture material 25 that binds indiscriminately to the many components (including the analyte) likely to be present in the sample. With regard to function, elements 24 and 25 are analogous to elements 15 and 17 respectively. Power source 21, electrical sensing means 23, and the electrical sensing circuits are shown and explained below in FIGS. 3A and 3B.

As depicted in FIG. 1B, an assay using LFIA 01 is initiated by placing onto sample pad 07 a small amount, e.g. a drop, of sample 27 suspected to contain the analyte for which the assay is designed. typically a drop of body fluid, such as blood, or a component thereof, e.g. plasma and serum. As the liquid components of sample 27 flow by capillary action (represented by the arrow in FIG. 1B) into test line 09 (see FIG. 1A for previously defined elements 01-25), analyte, symbolized by "stars" ("*"), 29 if present in sample 27, conjugates with antibodies 17 specific for that analyte, which are bound to aligned nanotubes 15 to form antibody-analyte complex 31. Complex 31 alters the electrical characteristics, i.e. signature, of close proximity array of fragments of nanotubes 15 bound just to antibodies 17. Typically, the electrical resistance of close proximity array of fragments of nanotubes 15 changes, which, in turn, changes the current and voltage passing through close proximity array of fragments of nanotubes 15. The observation of a change in the electrical signature of close proximity array of fragments of nanotubes 15 indicates that analyte is present in the sample.

Further, the amount of analyte present is related to the strength of the change of the electrical signature. Therefore, it is possible to prepare a standard curve by assaying multiple samples having known amounts of analyte, and comparing it to the magnitude of the change in electrical signature of the sample being assayed. This procedure of comparison to a standard curve as a method of quantitative measurement is well known in the art of biological assays.

Other components 33 of sample 27, symbolized by small triangles, i.e. other than analyte 29, comprising the sample also move by capillary action along with analyte 29 but do not conjugate with antibodies 17. Rather, they pass through test line 09 and conjugate with capture material 25 bound to aligned nanotubes 24 forming reference line 11 (see FIG. 1A) to form complex 35. The observation of a change in the electrical signature of close proximity array of fragments of nanotubes 24 indicates that the assay is complete and valid. The electrical circuitry and sensing means associated with close proximity array of fragments of nanotubes 24 forming reference line 11 is essentially the same as described below (see FIGS. 3A and 3B) for test line 09. Components not capture at test line 09 or reference line 11, e.g. liquids such as water along with minerals (symbolized by small circles ("o"), continue to flow by capillary action and are absorbed into wicking pad 13. FIG. 1C shows the present system at the completion of an assay (refer to FIGS. 1A and 1B for the previously identified elements).

The present LFIA 01 and all the elements thereof described above optionally may be housed in a protective cassette as is often done the LFIA art. The cassette is typically plastic, but may be of glass, rubber, polymer coated paper, or similar material. Typically, the cassette has an opening above sample pad 07 to allow a liquid sample to be applied, and openings or transparent windows above test line 09 and reference line 11 to allow observation of these lines. Note that in the present invention, the detection is by electrical means, so an opening for visual observation is not required. The cassette optionally may be imprinted with directions and related information.

In FIGS. 2A, 2B, and 3A-3C, a more detailed schematic presentation of nanotube band lines are shown, and in FIG. 3C detection principles are illustrated. A solution of close proximity array of fragments of nanotubes 15/antibody 17 conjugate is loaded into nitrocellulose membrane 05 as the test line 09 (FIG. 2A) where nanotubes 15 are mixed and linked together in nanotube band 41. Likewise, close proximity array of fragments of nanotubes 24/capture material 25 conjugate is loaded to form reference line 11 where close proximity array of fragments of nanotubes 24 are mixed and linked together in nanotube band 43. FIG. 2B presents a cross sectional view (perpendicular to the longitudinal axis) of the present LFIA illustrating nanotube bands 41 and 43 in relationship to sample pad 07 and wicking pad 13.

FIG. 3B presents a cross sectional schematic view of the present LFIA illustrating the electrical measurements across nanotube band 41. This view is along the longitudinal axis cutting through close proximity array of fragments of nanotubes 15 conjugated to antibodies 17, i.e., nanotube band 41, and is directly analogous to a view of nanotube band 43. Power source 21 is symbolic represented as a battery, and electrical sensing means 23 is symbolic represented as an electrical meter such as a volt or amp meter. FIG. 3A depicts nanotube band 41 to which is conjugated antibodies 17. After electrodes 45 are installed (FIG. 3B), the test strip is ready to use. For FIG. 3C, a small volume of sample containing antigen (biomarkers) is added to sample pad 07, which will flow to the absorbent pad. When the solution is passing through the nanotube test lines, material captured on the surface of the nanotubes, which produces conductivity/resistance change. Compared with normal nanotube band without biomarker binding (FIG. 3B), when the antigens bind to the antibody located in the surface of the nanotube device (FIG. 3C), the resistance of nanotube device will be increased. The changes are correlated to the concentration of analyte 29 present in the sample.

Again referring to FIGS. 3B and 3C, the skilled artisan in electronics will appreciated that a simple measuring device such as a volt or amp meter could readily be replaced as electrical sensing means 23 in the above illustration with a sophisticated electronic detection system employing a computer. Such a computer based system could not only detect the presents of an analyte, but rapidly and accurately analyze data from the detection means. For example, a computer based system could digitally compare input data from the assay with stored standardized data then graphically display the results of the assay. Further, a computer bases system could catalogue and store data from multiple assays to analyze assays over time. It is such a computer based detection system that is contemplated for the present invention.

Preparation of Nanotubes with Biomarker Sensing Properties

One of key steps for nanotube based biomarker sensing is the conjugation process. The present method uses commercially available single wall carbon nanotubes (SWNT) the surfaces of which are modified with multiple carboxylic acid functions (SWNT-COOH) 1 as shown in Scheme 1. (For simplicity, only portion of one SWNT and one —COOH group is illustrated.) Nanotube (SWNT_COOH) 1 is treated with EDC and NHS in DMF at room temperature for one hour, which yields intermediate compound 2, in which the carboxy function is activated by NHS. Compound 2 is then conjugated with antibody mAb producing compound 3 (SWNT-mAb). The antibody mAb selected is specific for the analyte for which the assay is intended. To reduce non-specific binding, the nanotube is coated with a polymer to yield coated SWNT-mAb 4. That is, the polymer coat insulates the outer shell of the nanotube. A detailed teaching of the process of Scheme 1 is provide hereinbelow in Example 1

Scheme 1 Preparation of coated nanotube-mAb conjugate through covalent method

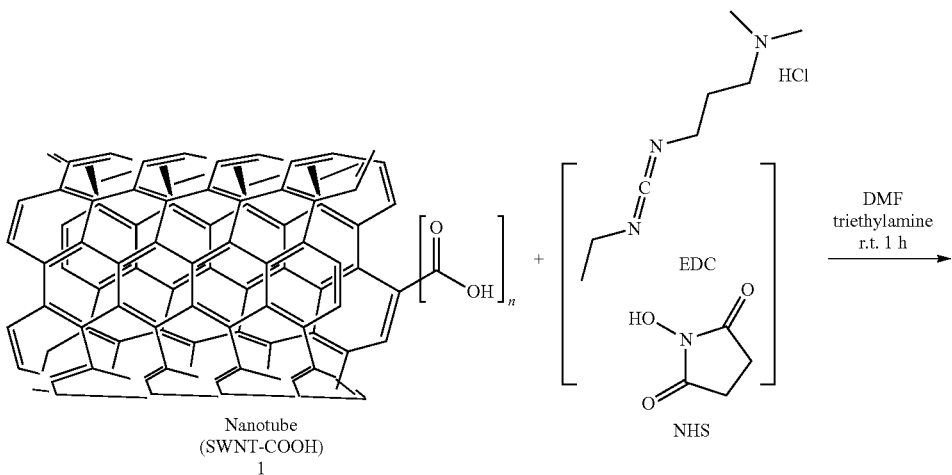

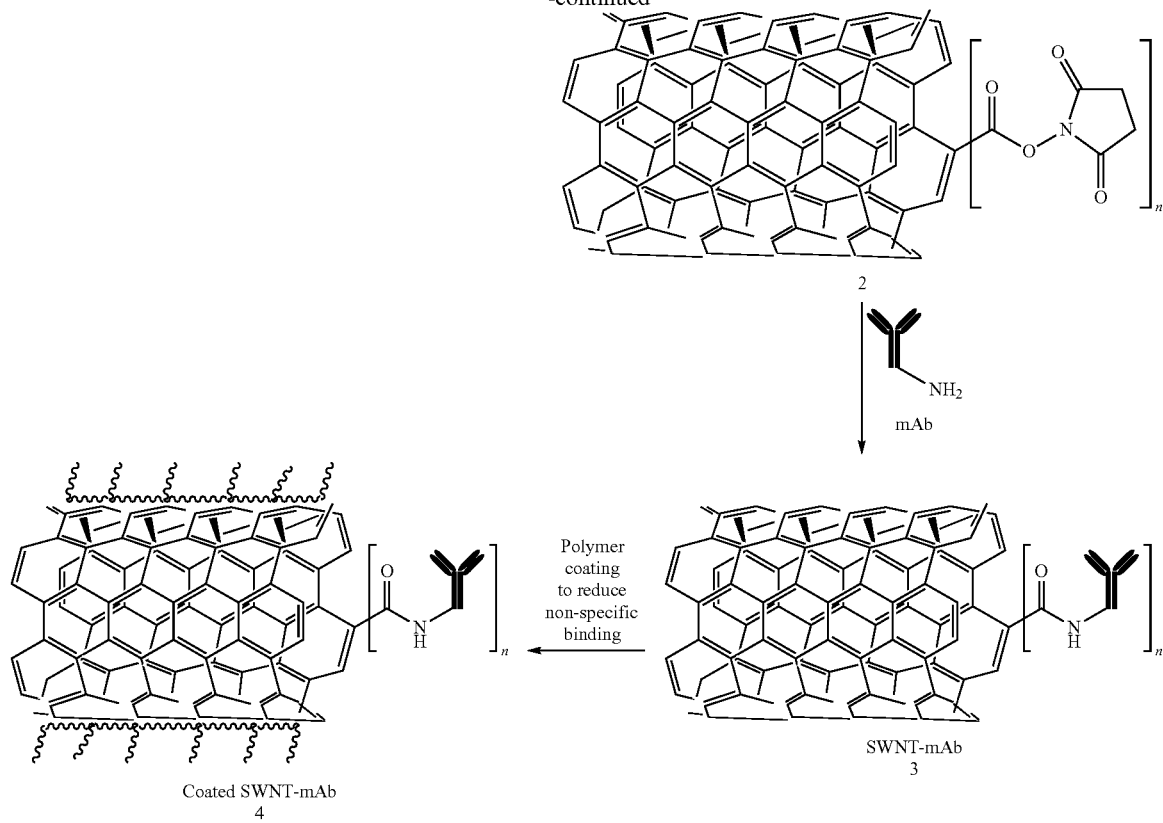

Assemble of Lateral Flow Assay System

The LFIA cards, or strips of the present system may be prepared by any of the methods well known in the art from commercially available materials. For example, David Carlberg, "Lateral-flow Assays: Designing for Automation," *IVD Technology*, (Cover Story) May 1999, teaches methods of LFIA preparation suitable for large scale, automated manufacturing of LFIA systems. The nanotube bands novel in the present invention may by imprinted onto the LFIA cards using Inkjet printing technology. A detailed teaching of the preparation of the LFIA system of the present invention is provide hereinbelow in Examples 2 and 3.

EXAMPLES

The following abbreviations are used herein:

| Abbreviation | Full name |
|---|---|
| SWNT | Single wall carbon nanotube |
| SWNT-COOH | Single wall carbon nanotube which surface contain carboxy groups |
| NHS | N-Hydroxysuccinimide |
| BST | 50 mM borate buffer pH 9.0 containing 0.05% Tween-20 |
| PBS | Phosphate buffered saline |
| DMF | Dimethylformamide |
| WMCO | Molecular weight cut off |
| PBA-NHS | pyrenebutanoic acid succinimidyl ester |
| CRP | C-reactive protein |
| mAb | Monoclonal antibody |
| EDAC | Other abbreviation: EDC or EDCI Chemical name: 1-ethyl-3-(3-dimethylaminopropyl) carbodiimide, commonly obtained as the hydrochloride, is a water soluble. |
| TAPS | N-Tris(hydroxymethyl)methyl-3-aminopropanesulfonic acid, Molecular formula: $(HOCH_2)_3CNHCH_2CH_2CH_2SO_3H$, which is a chemical to make buffer. |
| Tris | Tris(hydroxymethyl)aminomethane, with the formula $(HOCH_2)_3CNH_2$, which is a chemical to make buffer. |

Example 1: Conjugation of SWNT-COOH and Antibody mAb

Step 1: Preparation of Stock Solution of SWNT-COOH 50 mg SWNT-COOH (Cat#DL1.5L1-5-COOH, vendor: Nanolab, Inc., Waltham, Mass.) was placed in a 2 mL plastic microcentrifuge tube, and mixed with 1 mL of 0.1% KOH contained 0.1% Tween-20. The suspension was then sonicated for 5 minutes. The tube was centrifuged for 2 minutes at 5,000 rpm. The upper layer solution was taken and placed in another 5 mL plastic container. The insoluble material was then mixed with 1 mL of 0.1% KOH, and the above procedure was repeated 4 times. The upper layer solutions were combined and the total volume was 5.0 mL. The insoluble nanotube was then dried under vacuum. The residue was found to have weight of 35 mg. Thus the nanotube solution concentration was 15 mg/5 mL=3.0 mg/mL. This solution was centrifuged to remove the upper layer solution at 13,000 rpm for 15 minutes. The residue was then mixed with 1.5 mL sodium borate 50 mM, pH 9.0, which gave SWNT-COOH solution at 10 mg/mL.

Step 2: Activation of Carboxy Groups Attached to the Nanotubes 0.2 mL (2.0 mg, stock concentration 10 mg/mL) SWNT-COOH solution prepared as in Step 1 was mixed with 0.6 mL PBS (10× concentration, pH 7.4) contained 0.1% Tween-20. Then 0.1 mL EDAC (20 mg, fresh prepared stock solution 200 mg/mL in PBS 10×, pH 7.4) (Note: EDAC stock solution must be prepared freshly since EDAC stock solution is not stable in aqueous solution) was added to the black suspension. The mixture was vigorously mixed using a vortex mixer. A solution of 0.1 mL NHS (10 mg, stock solution 100 mg/mL in DMF) was then added at once (Note: NHS stock solution is recommended to prepare freshly). The mixture was gently mixed for 30 minutes at room temperature. Next, the mixture was then purified by centrifuging at 8,000 rpm for 3 min. The supernatant was discarded and the black residue at the bottom was re-constituted with 1.0 mL BST buffer (20 mM pH 8.0 borate with 0.5% tween-20). The black suspension was briefly vertexed for 10 seconds and sonicated for 1 min, before it was centrifuged at 8,000 rpm for 3 min. The supernatant was discarded and the black residue at the bottom was re-constituted with 1.0 mL, which corresponded to SWNT-COOH 2.0 mg/mL.

Step 3: Antibody Conjugation Reaction

The NHS ester functionalized carbon nanotubes SWNT-COOH in BST was mixed with 41 μL (0.1 mg) CRP mAb (stock concentration=2.42 mg/mL, Cat#6404-SP2, Biospacific). [Note: ratio of SWNT-COOH to CRP-mAb is 20:1 (w/w)]. The mixture was then gently shaken overnight at room temperature.

Step 4: Quenching the Reaction and Blocking Non-Specific Binding Sites 0.1 mL PBS solution contained 0.1M 2-aminoethanol and 10% BSA was added to the black mixture from Step 3. The mixture was then gently shaken for 30 minutes at room temperature. This quenched the un-reacted NHS groups at surface of the nanotubes, and blocked the non-specific binding sites of the nanotubes.

Step 5: Purification of Nanotube Conjugate

The antibody-conjugated SWNT-COOH from Step 4 was centrifuged at 8,000 rpm for 2 minutes. The supernant was discarded, and the black residues was mixed with 1.0 mL borate buffer (20 mM, pH 8.0 with 0.1% sodium azide, and 0.05% tween 20). The suspension was centrifuged at 8,000 rpm for 2 minutes. The supernant was discarded and the black residues were then re-constituted with total 0.5 mL TMT buffer (50 mM Taps, 50 mg/mL maltitol, 0.05% Tween-20, and 0.1% sodium azide), which contained SWNT-COOH 4.0 mg/mL.

Example 2: Methods of Assembling Lateral Flow Test Card

Materials used for assembling lateral flow test card are: (1) nitrocellulose membrane (05 in the Figures referenced above): (25 mm wide rolls) SHF0900425 (15 micron pore size), obtained from GMP-qualified manufacturer, Millipore, Inc), (2) Sample pad (07 in FIG. 2)/Conjugate pad: Grade 8975 (or equivalent) fiberglass pad (20 mm wide rolls) provided by Pall, Inc. (3) wicking pad (absorbing pad) membrane (13 in FIGS. 1A-1B, 2A, and 2C referenced above): Ahlstrom 222 (or equivalent) thick absorbent pad (25 mm wide rolls) supplied by Ahlstrom; (3) plastic-backed adhesive card membrane support (03 in the Figures described above): 60 mm×300 mm G&L Precision Cutting, LLC. (4) cassette: Plastic 4.5 mm wide channel (60 mm length) single-strip cassette (Princeton BioMeditech Corp, PBMC, NJ)

Typical assembly procedure:

(a) Remove the paper cover of the plastic-backed adhesive cards (60 mm×300 mm) to expose the adhesive side of the cards. Take the card, and with the exposed adhesive-side face-up, place onto an assembler with a vacuum to hold to card in place.

(b) Take the nitrocellulose membrane, "nitro", and with the shiny side facing down (membrane-side face-up), carefully place the nitro strip into place onto the exposed-adhesive card so that the bottom of the nitro is approximately 17-18 mm from the bottom of the card (or as indicated from the final R&D protocols). Use one of the paper covers from the previous step (covered the adhesive side of the card prior to removal) to carefully and gently lay on top of the very fragile nitro, and then gently press along the length of the nitro strip to ensure proper adhesion.

(c) Take the absorbent pad, pre-cut to 300 mm long from a larger roll (25 mm wide), and align to the top of the card and press into place, thereby overlapping the top edge of the nitro (already adhered into place in the previous step) by 2-5 mm. This overlap is important for the assay to work properly.

(d) Take the conjugate pad (10 mm×300 mm), if the final product requires a separate conjugate pad from the sample pad, and place at the bottom edge of the nitro so that it overlaps the nitro by 2-5 mm, while the rest of the conjugate pad adheres to the exposed adhesive. Press firmly into place.

Example 3: Making Nanotube Test Lines on the Membrane

Method 1: using Inkjet printing technology:—commercial printers such as DIMATIX Fujifilm DMP-2831 and Hewlett-Packard Deskjet K7108 are used to dispense the nanotube suspension into nitrocellulose membrane in the lateral flow test card described example 2.

Method 2: using Isoflow (trademark) reagent dispensing equipment:—commercial available equipment such as Isoflow (trademark) reagent dispensing equipment (vendor: Imagene Technology) is used to make the nanotube test line on nitrocellulose membrane in the lateral flow test card described example 2.

The electrodes that connect the electrical measuring components to the nanotubes (shown as in the Figures) in the form of a paste may be directly printed on the surface of nanotube test line and reference line with a commercial inkjet printer such as DIMATIX Fujifilm DMP-2831. Another strategy is to use shadow mask to evaporate Ti/Au electrodes on the strips first and then print conjugated nanotube onto test strip and its electrode to construct the sensor device. The shadow mask is composed of thousands of unit with two open windows to allow metal vapor depositing on the target area. Thus, thousands of devices may be fabricated in one e-beam evaporation process. In the approach, the electrodes are manufactured first and then biomarker conjugated nanotubes will be printed on to test strip. After electrode fabrication, a Kinematic Matrix Model #2360 (Terra Haute, Calif.) guillotine cutter, or similar device, may be used to cut the card to strips.

Example 4: Determination Low Concentration in Picogram/ml Range of CRP Antigen

To carry out the experiments, CRP antigen supplied by Biospecific, Inc. (Cat #J81600452), which is human CRP antigen high pure (99.2%, single band at 21 kd, determined by SDS-Page) was employed. The CRP antigen is first diluted in RB001 buffer solution which contained: 1% Tetronic 904, 0.1% PVP-10, 0.1% sodium azide and TE buffer 5×. Different CRP antigen concentrations were prepared for the experiments based on the requirement of concentration range.

In this experiment, electrodes were installed as described in the following:
  Metal wire as shadow mask
  E-Beam Evaporation for the fabrication of electrodes (Ti/Au=10 nm/200 nm)
  One sample (#2P49) was used for device fabrication
Test Procedures:
Step 1: Place 1 drop of pure water onto the nanotube-CRP-Mab test line on the lateral flow test strip. The surface of the membrane is then dried by a gentle flow of nitrogen gas across the surface. The resistance of the nanotube test line is measured and recorded.
Step 2: Place 1 drop of 5 pg/mL CRP antigen solution (formulated in RB001 buffer) onto the test line. The surface of the membrane is again dried by a gentle flow of nitrogen. The resistance of the nanotube test line is measured and recorded.
Step 3: Place 1 drop of pure water into the nanotube-CRP-Mab test line on the lateral flow test strip. The surface of the membrane is then dried by blowing nitrogen gas. The resistance of the nanotube test line was measured and recorded.
Step 4: Place 1 drop of 50 pg/mL CRP antigen solution (formulated in RB001 buffer). The surface of the membrane is then dried by blowing nitrogen gas. The resistance of the nanotube test line was measured and recorded.
Step 5: Place 1 drop of pure water into the nanotube-CRP-Mab test line on the lateral flow test strip. The surface of the membrane is then dried by blowing nitrogen gas. The resistance of the nanotube test line was measured and recorded.

This example demonstrates that the present invention is capable of detecting very low concentration of CRP antigen in the pictogram/mL range. For this example, the low level was at 5 pg/ml.

Example 5: Determination of Very Low Concentration in Sub Pictogram/ml Range of CRP Antigen In this example, CRP antigen concentrations was prepared in sub-picogram/mL range. The test procedures were as follows:
Step 1: Place 1 drop of pure water into the nanotube-CRP-Mab test line on the lateral flow test strip. The surface of the membrane is then dried by nitrogen gas. The resistance of the nanotube test line was measured and recorded.
Step 2: Place 1 drop of 0.1 pg/mL CRP antigen solution (formulated in RB001 buffer). The surface of the membrane is then dried by nitrogen gas. The resistance of the nanotube test line was measured and recorded.
Step 3: Place 1 drop of pure water into the nanotube-CRP-Mab test line on the lateral flow test strip. The surface of the membrane is then dried by nitrogen gas. The resistance of the nanotube test line was measured and recorded.
Step 4: Place 1 drop of 0.5 pg/mL CRP antigen solution (formulated in RB001 buffer). The surface of the membrane is then dried by nitrogen gas. The resistance of the nanotube test line was measured and recorded.
Step 5: Place 1 drop of pure water into the nanotube-CRP-Mab test line on the lateral flow test strip. The surface of the membrane is then dried by nitrogen gas. The resistance of the nanotube test line was measured and recorded.

Example 6: Enhancing the Detection Specificity of the Nanotube Device

Like any other binding measurement assay, the non-specific binding will affect detection specificity. For this work, it is necessary to take some measures to block the non-specific binding and increase detection specificity. In this example, the procedure is designed to reduce BSA non-specific binding when measuring very low CRP biomarker.
A. Blocking the Non-Specific Binding Sites of Nanotubes:
To block the non-specific binding site of the nanotube device, we designed the following experiment: nanotube CRP mAb conjugate lot #QC2P51 (CRP mAb was covalently bounded to the carboxy group at the surface of nanotube) at 100 μL (nanotube concentration: 4 mg/mL) was mixed with 10 μL BSA (stock concentration: 10 mg/mL in PBS, pH 7.4). The black suspension solution was gently shaken for 30 minutes at room temperature. The nanotube was then centrifuged at 10,000 rpm for 5 minutes. The clear buffer solution was drawn away using a pipette. The black residue was washed three times using PBS buffer as described in the following: the residue was first mixed with 1 mL PBS, pH 7.4, then vertexed and centrifuged at 10,000 rpm for 5 minutes. The solution was decanted. The purified nanotube was then re-constituted in 100 μL TMT buffer.
B. Loading Nanotube into the Membrane:
We manually loaded the nanotube conjugate into the membrane as described as the following:
Step 1:
  Pre-cut lateral flow test strips with 3 zones: top zone—absorbent pad (Alstrom #8964), middle zone—nitrocellulose (Millipore #SHF9004), low zone—conjugate pad (Alstrom#222): Strip dimension: 4 mm×60 mm, top zone ~20 mm, middle zone ~20 mm, low zone: ~20 mm.
Step 2:
  The above test strips were attached to an adhesive tape in a row.
Step 3:
  Using a long and soft pipette tip to load 6 μL nanotube solution. The tip was very carefully touched to the surface of the nitrocellulose membrane so that it could print a straight line.
Step 4:
  Labeling and drying the strip. The strips were labeled in the absorbent pad using water-resistant ink. The strips were then dried at 57° C. for 60 minutes, then stored in a desiccated bag.
  The nanotube device made the same as the previous procedure.
C. Installation of Electrodes:
  Fabrication of devices was described as the following:
  Metal wire as shadow mask
  E-Beam Evaporation for the fabrication of electrodes (Ti/Au=10 nm/200 nm)
  One sample (#2P76) was used for device fabrication
D. Experiment Procedures:
Step 1: Drop 1 drop of pure water into the nanotube-CRP-Mab test line on the lateral flow test strip. The surface of the membrane is then dried by blowing nitrogen gas. The resistance of the nanotube test line was measured and recorded.

Step 2: Drop 1 drop of 10 μg/mL BSA solution (formulated in RB001 buffer). The surface of the membrane is then dried by blowing nitrogen gas. The resistance of the nanotube test line was measured and recorded.

Step 3: Drop 1 drop of pure water into the nanotube-CRP-Mab test line on the lateral flow test strip. The surface of the membrane is then dried by blowing nitrogen gas. The resistance of the nanotube test line was measured and recorded.

Step 4: Drop 1 drop of 50 pg/mL CRP in RB001 buffer into the nanotube-CRP-Mab test line on the lateral flow test strip. The surface of the membrane is then dried by blowing nitrogen gas. The resistance of the nanotube test line was measured and recorded.

Step 5: Drop 1 drop of pure water into the nanotube-CRP-Mab test line on the lateral flow test strip. The surface of the membrane is then dried by blowing nitrogen gas. The resistance of the nanotube test line was measured and recorded.

E. Test Results:

A typical I-V graphic of the device is shown in FIG. *6a* when adding 10 μg/mL BSA. The test results are summarized in FIG. *6b* for 10 μg/mL BSA and 10 pg/mL CRP antigen.

This experiment showed that the resistant changes of the nanotube device upon interacting with 10 μg/mL BSA was small (~40 KQ), while that of the same nanotube device upon binding to 50 pg/mL CRP antigen was significantly larger (~270 KQ).

From the data, we can conclude that the non-specific bind from BSA existed. However, even with very high BSA concentration at 10 μg/mL, we were still able to detect low 50 pg/mL biomarker CRP concentration. The example demonstrates that the nanotube based lateral flow immunoassay of the present invention is very sensitive and also specific.

Buffers and Recipes

| Buffer name | Recipes and description |
|---|---|
| PBS 1X | Dissolve the following in 800 ml distilled H2O.<br>8 g of NaCl<br>0.2 g of KCl<br>1.44 g of Na2HPO4<br>0.24 g of KH2PO4<br>Adjust pH to 7.4 using 10% HCl or 10% NaOH<br>Adjust volume to 1 L with additional distilled H2O.<br>Sterilize by 0.2 uM membrane filtration. |
| PBS 10 X | Dissolve the following in 800 ml distilled H2O.<br>80 g of NaCl<br>2.0 g of KCl<br>14.4 g of Na2HPO4<br>2.4 g of KH2PO4<br>Adjust pH to 7.4.<br>Adjust volume to 1 L with additional distilled H2O.<br>Sterilize by autoclaving. |
| TE 100X | A 100 time concentrated buffer which contained tris and EDAC. A 100X concentrate TE buffer, when diluted to 1X, contains 10 mM Tris, 1 mM EDTA, pH ~8.0. |
| RB-001 | A buffer for running lateral flow test strips, which contained: 1% Tetronic 904, 0.1% PVP-10, 0.1% sodium azide and TE buffer 5X. |
| TMT | A buffer solution containing: 50 mM Taps, 50 mg/mL maltital, 0.05% Tween-20, and 0.1% sodium azide. |
| MGH | A buffer can stabilize and preserve the activity of CRP mAb/CRP antigen when loaded into the nitrocellulose membrane. Maltitol: 80 mg/mL, gelatin 20 mg/mL, HEPES 10 mM pH 8.0, sodium azide 0.1%. |
| MGH-02 | Two times concentrated MGH buffer, which contains Maltitol: 160 mg/mL, gelatin 40 mg/mL, HEPES 20 mM pH 8.0, sodium azide 0.2%. |
| BST | 50 mM borate buffer pH 9.0 containing 0.05% Tween-20 |
| PBST | 5X PBS buffer, pH 7.4 with 0.05% Tween-20 |
| HSTT | HEPES: 50 mM, pH 7.4<br>Sucrose: 10%<br>Trehalose: 5%<br>TW20: 0.05%<br>NaN3: 0.1% |

What we claim is:

1. A lateral flow immunoassay device comprising a lateral flow test strip, one or more arrays comprising a band of piled small fragments of single wall carbon nanotubes, to which are conjugated antibodies for a specific biomarker, wherein the fragments are in proximity to each other so that each fragment touches adjacent fragments sufficiently so that each array is capable of conducting an electric current, and the device is capable of detecting the presence of an amount of the biomarker at picogram/mL and femtogram/mL concentrations in a biological sample.

2. The device of claim 1, wherein:
   a) the lateral flow strip has a sample pad and a wicking pad distal to the sample pad, and wherein the one or more arrays comprise
   b) a first array of fragments of single wall carbon nanotubes to which are conjugated antibodies to the biomarker to be assayed, wherein the first array forms a test line proximal to the sample pad, and
   c) a second array of fragments of single wall carbon nanotubes to which are conjugated nonspecific antibodies, wherein the second array forms a control line adjacent to the first array and on a side of the first array opposite the sample pad.

3. The device of claim 2, further comprising a power source to pass electric current through the first and second arrays independently and a system for independently measuring changes in the current in the two arrays.

4. The device of claim 3, further comprising an electronic reader.

5. The device of claim 2, wherein the lateral flow strip comprises a backing film, in which a piece of sample pad and absorbent pad are laminated at each end of the strip and a piece of membrane is laminated in the middle, and the first carbon nanotube array is immobilized in the membrane as the test line.

6. A method of detecting the presence of an amount of a biomarker using the lateral flow immunoassay device of claim 1, the method comprising:
   contacting the lateral flow strip with a sample;
   flowing the sample over the one or more arrays; and
   detecting a change in the electric current in the one or more arrays to thereby detect the presence of an amount of the biomarker.

7. A method of using an array comprising a band of piled fragments of single wall carbon nanotubes as a biosensor for a lateral flow immunoassay, wherein the fragments are in proximity to each other so that each fragment touches adjacent fragments sufficiently so that the array is capable of conducting an electric current, the method comprising:

flowing a sample over the array, and detecting a change in an electric current in array to thereby detect an analyte in the sample.

8. A method of using biomarkers conjugated to an array comprising a band of piled fragments of single wall carbon nanotubes as a biosensor for lateral flow immunoassay, wherein the fragments are in proximity to each other so that each fragment touches adjacent fragments sufficiently so that the array is capable of conducting an electric current, the method comprising:

flowing a sample over the array; and detecting a change in an electric current in array to thereby detect an analyte in the sample.

9. The device of claim 3, further comprising a cassette.

10. The device of claim 9, where the cassette comprises a cover and a lateral flow strip holder.

11. The device of claim 10, wherein microelectrodes are pre-installed into the cover of the cassette, allowing contact with the nanotube test line on the membrane of the lateral flow strip.

\* \* \* \* \*